US009453827B2

(12) United States Patent
Maisonnier et al.

(10) Patent No.: US 9,453,827 B2
(45) Date of Patent: Sep. 27, 2016

(54) POOL SURVEILLANCE SYSTEM AND ASSOCIATED SURVEILLANCE METHOD

(71) Applicant: ALDEBARAN ROBOTICS S.A, Paris (FR)

(72) Inventors: Bruno Maisonnier, Paris (FR); Fabien Bardinet, Issy-les-Moulineaux (FR)

(73) Assignee: ALDEBARAN ROBOTICS, Paris (FR)

( * ) Notice: Subject to any disclaimer, the term of this patent is extended or adjusted under 35 U.S.C. 154(b) by 0 days.

(21) Appl. No.: 14/359,523

(22) PCT Filed: Nov. 20, 2012

(86) PCT No.: PCT/EP2012/073102
§ 371 (c)(1),
(2) Date: May 20, 2014

(87) PCT Pub. No.: WO2013/076076
PCT Pub. Date: May 30, 2013

(65) Prior Publication Data

US 2014/0327548 A1 Nov. 6, 2014

(30) Foreign Application Priority Data

Nov. 21, 2011 (FR) ..................................... 11 60588

(51) Int. Cl.

| | |
|---|---|
| ***G08B 23/00*** | (2006.01) |
| ***G01N 33/18*** | (2006.01) |
| ***G08B 21/08*** | (2006.01) |
| *G08B 13/00* | (2006.01) |
| *G08B 21/00* | (2006.01) |
| *G08B 29/18* | (2006.01) |

(52) U.S. Cl.
CPC ......... *G01N 33/1886* (2013.01); *G08B 21/084* (2013.01); *G08B 29/188* (2013.01)

(58) Field of Classification Search
CPC .... G08B 21/088; G08B 23/00; G08B 21/00; G08B 13/22; B63C 9/0005
USPC ..................................... 340/603, 573.6, 565
See application file for complete search history.

(56) References Cited

U.S. PATENT DOCUMENTS 5,115,222 A * 5/1992 Peralta ................ G08B 21/084 340/566
6,154,140 A * 11/2000 Thorpe .................. B63C 11/02 340/573.6

(Continued)

FOREIGN PATENT DOCUMENTS

EP 1492069 A1 12/2004
WO 9956214 A1 11/1999

(Continued)

*Primary Examiner* — Jack K Wang
(74) *Attorney, Agent, or Firm* — Baker Hostetler LLP

(57) ABSTRACT

A system for surveillance of a pool containing a liquid such as water-comprises at least one first element comprising at least one submersible robot provided with standalone propulsion capabilities for propelling the robot in the pool, onboard of which robot is installed at least one sensor capable of producing at least one measurement of a quantity representative of at least one disturbance of the pool relative to a reference state, the first element being furthermore provided with communication capabilities for communicating, in the submerged position, with at least one second element, the system being configured to process, in processing means, the output of the at least one sensor and to trigger at least one action.

6 Claims, 4 Drawing Sheets

(56) References Cited

U.S. PATENT DOCUMENTS

| | | | | |
|---|---|---|---|---|
| 2004/0144699 | A1* | 7/2004 | Lin | C02F 1/688 210/85 |
| 2008/0106422 | A1 | 5/2008 | Sparks et al. | |
| 2008/0174441 | A1* | 7/2008 | Durand | G08B 21/084 340/573.6 |
| 2009/0027211 | A1* | 1/2009 | Cutler | G08B 21/088 340/573.6 |
| 2012/0024796 | A1* | 2/2012 | Fischmann | C02F 1/004 210/697 |
| 2012/0132544 | A1* | 5/2012 | Lawrence | G01N 27/302 205/782 |
| 2012/0145561 | A1 | 6/2012 | Coulon et al. | |

FOREIGN PATENT DOCUMENTS

| | | | |
|---|---|---|---|
| WO | 2004019295 | A1 | 3/2004 |
| WO | 2006027456 | A1 | 3/2006 |
| WO | 2007002530 | A2 | 1/2007 |
| WO | 2011003923 | A1 | 1/2011 |

* cited by examiner

POOL SURVEILLANCE SYSTEM AND ASSOCIATED SURVEILLANCE METHOD

CROSS-REFERENCE TO RELATED APPLICATIONS

This application is a National Stage of International patent application PCT/EP2012/073102, filed on Nov. 20, 2012, which claims priority to foreign French patent application No. FR 1160588, filed on Nov. 21, 2011, the disclosures of which are incorporated by reference in their entirety.

FIELD OF THE INVENTION

The field of the invention is that of systems for surveilling pools, such as swimming pools, comprising a sensor capable of producing a measurement representative of a disturbance of the pool relative to a reference state.

More particularly, the field of the invention is that of the devices for monitoring the quality of the water stored in the pool. The field of the invention is also that of the surveillance systems watching for the occurrence of an intrusion of an individual in the pool.

BACKGROUND

The pools, such as private or public swimming pools, are filled with a liquid such as water. The constant renewal of the water cannot be considered. However, the composition of the water is not stable and the quality of the water is likely to degrade. Now, it is necessary to ensure a certain usable comfort in order to comply with predetermined safety conditions. It is therefore routine practice to equip such pools with a water quality surveillance system. Such a system comprises sensors which can measure physico-chemical quantities representative of the quality of the water. The sensors are, for example, capable of measuring the temperature of the water, its pH, its conductivity, its oxidation-reduction potential (representative of the concentration of bactericide agent in the water, such as chlorine, bromine or active oxygen) in the water. The surveillance of the quality of the water makes it possible to trigger an appropriate treatment of the water. The current practice is to introduce suitable upkeep products, in appropriate quantities, in order to actuate a water oxygenation pump or else a water filtration device.

WO 2007/02530 discloses a floating surveillance system with a sensor installed capable of measuring a quantity representative of the quality of the water. However, the rate of false alarms with this type of device is high. The measurement of the quality of the water at a particular point of the pool is not necessarily representative of the quality of the water in the pool as a whole.

An immersion surveillance system is known which is installed on the side of the pool and includes a probe that is dipped into the water capable of detecting an acoustic wave generated by a body falling into the pool. However, the number of false alarms (detection of immersion without immersion event or absence of detection of immersion when an immersion event has occurred) is high. For example, taking into account the force of the wind, the damping of the swell provoked by a falling body can take some time, even not occur when the speed of the wind is greater than 36 km/h. This phenomenon degrades the sensitivity of the system.

SUMMARY OF THE INVENTION

The aim of the present invention is to propose pool surveillance systems which are reliable, that is to say which exhibit a low false alarm rate.

To this end, the subject of the invention is a system for surveilling a pool containing a liquid such as water, characterized in that it comprises at least one first element comprising at least one submersible robot provided with standalone propulsion capabilities for propelling said robot in said pool and being provided with communication capabilities for communicating, in the submerged position, with at least one second element making it possible to communicate with said second element, said first element comprising a plurality of submersible robots and/or said second element being a submersible robot, sensors capable of producing measurements of a quantity representative of at least one disturbance of said pool relative to a reference state being installed onboard said submersible robots, the system being configured to process, in processing means 11, the outputs of said sensors (15, 150) to trigger at least one action of information on the disturbance of the pool relative to a reference state by means of information means.

This system exhibits enhanced reliability compared to the prior art systems.

Advantageously, the surveillance system also comprises an alarm device capable of producing a visual or audible alarm and/or display means.

Advantageously, the information means comprise means for modifying the external appearance of at least one submersible robot.

Advantageously, the second element is a central unit configured to float on the liquid contained in said pool.

Advantageously, the processing means are installed on the central unit.

Advantageously, at least one disturbance is an intrusion of an individual in the pool and in which said at least one sensor is also capable of detecting the intrusion of an individual in the pool.

Advantageously, said at least one sensor comprises two individual sensors spaced apart from one another so as to make it possible to locate the area of an intrusion detected by said at least one sensor, the system comprising means for detecting an area of immersion on the basis of the signals from the two individual sensors.

Advantageously, at least one disturbance is created by a modification of a physico-chemical parameter of the liquid contained in the pool above a reference threshold relating to said parameter.

Advantageously, the processing means comprise estimation means capable of producing, on the basis of measurements of a physico-chemical parameter of said liquid from a plurality of submersible robots, an estimation of the value of said physico-chemical parameter and means for evaluating the quality of said liquid capable of checking whether said liquid complies with a predetermined quality criterion by comparing at least one estimation of the value of said physico-chemical parameter with a reference threshold relating to said physico-chemical parameter.

Advantageously, the processing means also comprise means capable of generating an information means driving command on the basis of at least one estimation, or else on the basis of an evaluation of the quality of said liquid, so as to inform an individual of the quality of said liquid.

Advantageously, the first element comprises a number of submersible robots provided with standalone propulsion capabilities and onboard which are installed sensors capable of producing at least one measurement of a quantity representative of at least one disturbance of said pool relative to a reference state and/or the second element consists of a submersible robot provided with standalone propulsion capabilities and onboard which is installed at least one sensor capable of producing at least one measurement of a quantity representative of at least one disturbance of said pool relative to a reference state and in which the estimation means are capable of producing an estimation of the value of a physico-chemical parameter representative of the quality of said liquid on the basis of a plurality of measurements of said physico-chemical parameter from a plurality of submersible robots.

Advantageously, the estimation means are capable of producing an estimation of the value of a physico-chemical parameter representative of the quality of said liquid, based on a plurality of measurements of said physico-chemical parameter from one and the same submersible robot.

Also the subject of the invention is a method for surveilling a pool containing water based on at least one first element comprising at least one submersible robot provided with standalone propulsion capabilities for propelling said robot in said pool and being provided with communication capabilities for communicating, in the submerged position, with at least one second element making it possible to communicate with said second element, said first element comprising a plurality of submersible robots and/or said second element being a submersible robot, sensors capable of producing measurements of a quantity representative of at least one disturbance of said pool relative to a reference state being installed onboard said submersible robots, said method comprising a step of producing measurements of a quantity representative of at least one disturbance of said pool relative to a reference state, said measurements being obtained from said sensors, a step of communication of said first element in the submerged position with at least one second element, a step of processing the outputs of said sensors, to trigger at least one action of information on the disturbance of the pool relative to a reference state by means of information means.

Advantageously, the second element is a submersible robot provided with standalone propulsion capabilities for propelling said robot in said pool, on which is installed at least one sensor capable of producing at least one measurement of a quantity representative of at least one disturbance of said pool relative to a reference state, said system being also configured to process, in the processing means, the output of said at least one sensor installed on said second element.

Advantageously, said at least one sensor is also capable of detecting the intrusion of an individual in the pool and in which, the first element comprises a plurality of submersible robots and/or the second element consists of a submersible robot.

Advantageously, the method comprises:

- a step of detection of an intrusion of a body in the water upon which said at least one sensor produces, when it detects the intrusion of an individual in the water, a first alert signal A1 and a first probability signal PA1, PB1, PC1 representative of the probability with which the intrusion is likely to have actually occurred,
- and, when a first alert signal A1 is produced by a first submersible robot, a confirmation step upon which a check is carried out, at least on the basis of a probability signal from at least one second submersible robot, to check whether the intrusion of an individual is confirmed by at least one second submersible robot.

Advantageously, when the intrusion is confirmed, an information means driving step so as to inform an individual that an individual has fallen into the water of the pool.

Advantageously, the confirmation step comprises:

- a first step of comparison of the number of submersible robots N having produced a first alert signal A1 with a predetermined threshold number,
- and, when the number of submersible robots N having produced a first alert signal A1 is at least equal to the predetermined threshold number, a second step of comparison of first probability signals PA1, PB1, PC1, associated with the respective alert signals A1, with a first predetermined probability threshold S1.

Advantageously, the confirmation step comprises, when at least one probability signal is below the first predetermined threshold, respectively when the number of submersible robots having produced a first alert signal Al is less than the predetermined threshold number,

- a step of identification of a main submersible robot corresponding to the submersible robot from which the first probability signal with the highest value was obtained,
- a step of actuation of the driving means of at least one other submersible robot, corresponding to a submersible robot other than the main submersible robot, so that it approaches the main submersible robot,
- a second detection step during which said sensor installed onboard said at least one other submersible robot produces a probability signal representative of the probability with which the intrusion is likely to have really occurred,
- a third comparison step during which said at least one second probability signal is compared with a second probability threshold.

Advantageously, the intrusion event being confirmed when at least one second probability signal is above the second predetermined threshold.

Advantageously, the threshold number is equal to three.

BRIEF DESCRIPTION OF THE DRAWINGS

Other features and advantages of the invention will become apparent on reading the following detailed description, given as a nonlimiting example and with reference to the attached drawings in which.

DETAILED DESCRIPTION

From one figure to another, the same elements are identified by the same references.

Figure 1:
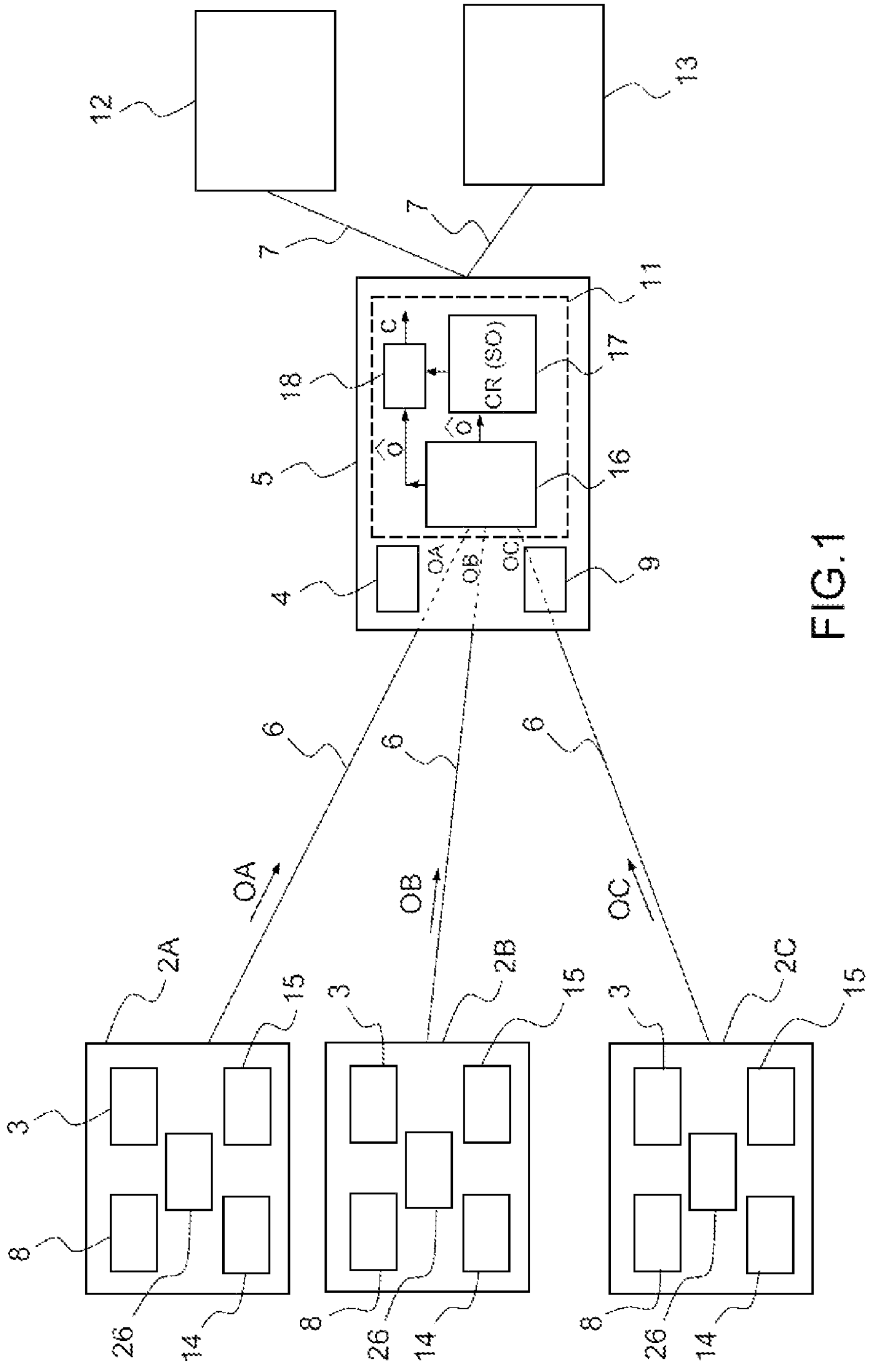
FIG. 1 schematically represents a system according to a first embodiment of the invention, FIG. 2 schematically represents a system according to a second embodiment of the invention.
Figure 2:
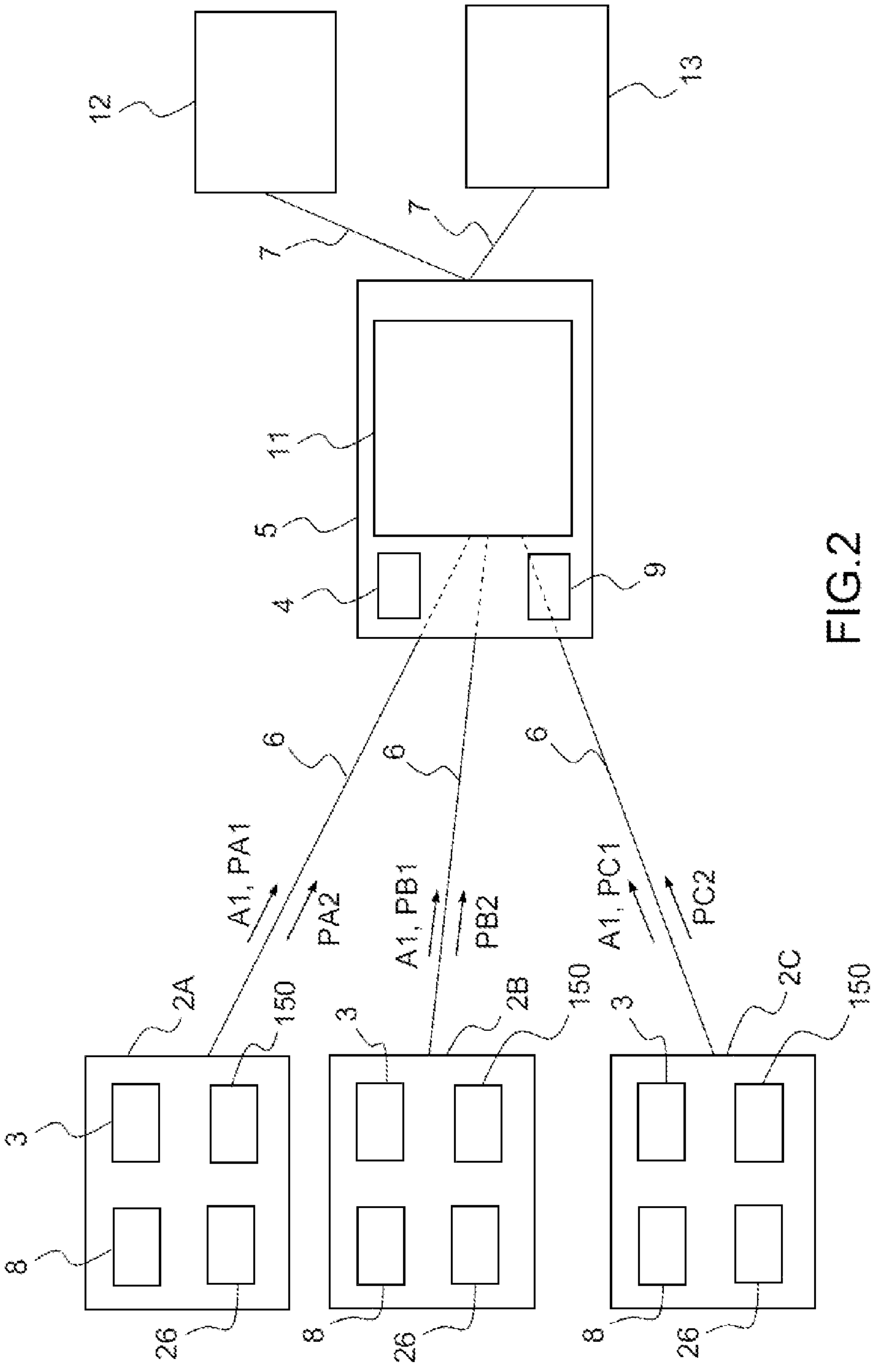

FIGS. 1 and 2 schematically represent two different embodiments of a system for surveilling a pool according to the invention. In these embodiments, the liquid contained in the pool is water. Everything which is described hereinafter in the text is also valid for any other transparent liquid.

The system according to the first embodiment represented in FIG. 1 is a system for surveilling the quality of the water stored in the pool.

The system according to the second embodiment represented in FIG. 2 is a system for surveilling the occurrence of an intrusion of an individual in the water stored in the pool. The elements common to both embodiments will be described first.

The surveillance systems according to the two embodiments represented comprise a first element consisting of three submersible robots 2A, 2B, 2C provided with standalone propulsion capabilities 3. The submersible robots are able to move freely in the water.

The standalone propulsion means 3 are configured to communicate movements to the submersible robots 2A, 2B, 2C in all three dimensions in the water.

Advantageously, the submersible robots are submarine robots. They are configured to be submerged and to navigate at depth.

The propulsion means 3 are, for example, arranged to communicate, to the submersible robots, movements similar to those of fish.

The systems according to the invention also comprise means 4 for actuating the propulsion means 3. In the embodiments represented, the actuation means 4 are remote and installed on a second element consisting of a central processing unit 5. The central processing unit 5 is configured to float on the water of the pool.

As a variant, the actuation means 4 are installed onboard the submersible robots 2A, 2B, 2C. The submersible robots are then able to move independently in the liquid medium. The actuation means 4 can also be installed onboard one of the submersible robots, which is then the master robot.

The floating central unit 5 has various equipment installed in it which will be described later. This arrangement makes it possible to eliminate the time it takes to install the equipment installed onboard the floating central unit on the structure of the pool.

The first element, consisting of three respective submersible robots 2A, 2B, 2C, is provided with communication capabilities for communicating in an immersed position and advantageously submerged position, with the floating central unit 5 and/or with the other respective submersible robots 2A, 2B, 2C.

These communication capabilities enable the floating central unit 5 and the submersible robots 2A, 2B, 2C to communicate via wireless link means 6. They enable the central unit 5 to remotely control the propulsion means 3.

The wireless link means are, for example, a transmitter and a receiver of seismic, acoustic, optical (infrared or visible) or any other type suitable for transmitting data in a liquid medium, in particular in water. The transmission of data by means of very low frequency acoustic waves or infrared or visible electromagnetic waves is particularly suited to the invention. Very low frequency waves, called VLF, with a frequency of between 3 and 30 HZ, can be transmitted virtually without attenuation in a liquid medium. Conversely, the radiofrequency ranges RF are almost entirely absorbed by the liquid medium where the propagation of these waves is extremely limited.

The submersible robots 2A, 2B, 2C comprise energy accumulation means 8 capable of supplying electrical power to the equipment installed onboard said robots 2.

Electrical energy power supply means 9 intended to cooperate with the energy accumulation means 8 to ensure that they are recharged, for example by induction, are installed onboard the central unit 5.

Advantageously, the actuation means 4 are configured in such a way as to direct the submersible robots 2A, 2B, 2C toward the central processing unit 5 to make the power supply means 9 cooperate with the accumulation means 8 so as to ensure that they are recharged, when the electrical energy stored in the accumulation means is below a predetermined energy threshold. The first element consists, in the embodiments of FIGS. 1 and 2, of the three submersible robots 2A, 2B, 2C provided with standalone propulsion capabilities and on which are installed sensors 15, 150. The sensors 15, 150 are capable of producing measurements of a quantity representative of at least a disturbance of the pool relative to a reference state.

Advantageously, the robots comprise three-dimensional location capabilities which are not represented. These locations capabilities advantageously comprise means 26 for locating the robot in three dimensions. Such means 26 can, for example, be an inertial central unit.

As a variant, the location capabilities of a submersible robot comprise communication capabilities for communicating with at least one submersible robot and/or the central processing unit 5. The processing means 11 (described below) are then configured to position the robots on the basis of communication signals from the communication capability, for example by triangulation.

The system is configured to process, in processing means 11, the outputs of the sensors 15, 150, and, possibly, location capabilities, and trigger at least one action.

The actions triggered can, for example, be actions of informing an individual of the disturbance of the pool relative to a reference state.

The processing means 11 are capable of generating commands for driving the information means 12, 13, 14 by using measurements of the quantities representative of at least a disturbance of the pool relative to a reference state and possibly location capabilities.

The processing means 11 are remote. They are installed onboard the central unit 5. As a variant, the processing means are installed onboard a submersible robot.

The information means comprise, in both the embodiments, display means 12 arranged outside the pool. The displays means are, as a variant, installed on the central unit 5.

The information means also comprise an alarm device 13. This device is, for example, capable of producing a visual or audible alarm. The alarm device can be remote. It can be installed outside the leisure pool.

The system also comprises communication means 7 making it possible to exchange data between the processing means 11 and the respective information means 12, 13, 14. These communication means are, for example, wireless links.

There now follows a more precise description of the system for surveilling the quality of the water represented in FIG. 1.

In this embodiment, "disturbance of the pool" should be understood to mean a disturbance created by a modification of a physico-chemical parameter of the water, above a reference threshold. The expression "disturbance of the water contained in the pool" therefore applies.

The sensors 15 are capable of producing measurements of a physico-chemical parameter of the water.

These physico-chemical parameters are quantities representative of the quality of the water in which the submersible robot is submerged.

The sensors 15 are, for example, capable of producing measurements OA, OB, OC of the oxidation-reduction potential of the liquid medium in which the submersible robot is submerged. The oxidation-reduction potential is representative of the concentration of disinfectant (chlorine, bromine, active oxygen) in the water.

As a variant, the sensor is a thermometer, or else a sensor capable of measuring the pH or the conductivity of the aqueous medium in which the sensor is submerged.

As a variant, the submersible robots have a plurality of sensors 15 installed, capable of measuring different physico-chemical quantities of the quality of the water.

As a variant, the system comprises 1, 2 or more than 3 submersible robots.

The information means comprise, for example, installed information means 14 capable of modifying the visual appearance of the submersible robots based on a command from the processing means 11.

The installed information means 14 comprise light-emitting diodes.

The light-emitting diodes are arranged in such a way as to produce a lighting that is visible from the outside of the submersible robots. They are, for example, installed on the surface of the submersible robots. They can also be installed inside a box delimiting the submersible craft, said box being transparent to the visible electromagnetic radiation.

These means 14, not represented in FIG. 2, could be installed on the submersible robots of the system according to the second embodiment.

The processing means 11 comprise estimation means 16 capable of producing, on the basis of at least one measurement of a physico-chemical parameter of the water, an estimation of the value of said physico-chemical parameter.

The processing means 11 also comprise means 17 for evaluating the quality of the water capable of checking whether the water complies with a predetermined quality criterion CR by comparing at least one estimation of the value of the physico-chemical parameter with a reference threshold relating to the parameter concerned.

In the case where several sensors are installed onboard one and the same robot, the means 17 receive estimations of several quantities. The water quality criterion can be a composite quality criterion. The means 17 then compare the evaluations of the values of several measured physico-chemical parameters with respective predetermined thresholds. This amounts to evaluating the quality of the water on the basis of measurements of several quantities. It makes it possible to improve the reliability of the device.

In the embodiment represented in FIG. 1, the action generated by the system is an action to inform an individual.

The processing means 11 also comprise means 18 for generating a command C for driving the information means 12, 13, 14 on the basis of at least one estimation of the value of at least one physico-chemical parameter representative of the quality of the water or else on the basis of the evaluation of the quality of the water produced by the evaluation means 17.

According to one mode of operation of the device according to the invention, the sensors 15 installed onboard the submersible robot produce measurements OA, OB, OC of the oxidation-reduction potential. What follows below is also valid when another type of physico-chemical parameter is measured.

These measurements are performed regularly. These measurements are transmitted regularly to the processing means 11 by means of the first communication means.

The estimation $\hat{O}$ of the value of the oxidation-reduction potential is calculated on the basis of several measurements of this potential produced by a single sensor. It is, for example, an average of a plurality of measurements OA produced by a sensor 15 at different instants.

The evaluation means 17 then receive an estimation $\hat{O}$ of the oxidation-reduction potential. They compare this estimation $\hat{O}$ to a predetermined oxidation-reduction threshold SO. If the potential is above, respectively below, this threshold, this means that the concentration of disinfectant agent is insufficient, respectively sufficient. The means 18 for generating a command then generates a command to switch on a diode emitting red light, respectively green light. The owner of a swimming pool, seeing the submersible craft emit a red light, then knows that he or she has to pour disinfectant into the swimming pool.

The means 18 can also generate a command to trigger an alarm or a display command.

By estimating the oxidation-reduction potential on the basis of several measurements produced at different instants, there is an assurance that the estimation of the oxidation-reduction potential is accurate. The surveillance system is then reliable. In other words, the number of false alarms from this system is low. An operator or an owner can trust the color of the submersible robots to know when to supply the water of the pool with disinfectant.

Advantageously, the submersible robots are configured to permanently move around. Calculation of the oxidation-reduction potential is then produced on the basis of measurements taken at different points of the swimming pool, which enhances the accuracy of the estimation of the potential and the reliability of the system according to the invention.

As a variant, the estimation $\hat{O}$ of the value of the oxidation-reduction potential is calculated on the basis of measurements of this potential produced by different sensors installed on different submersible robots (the system then comprises at least two submersible robots). It is, for example, calculated by producing the mean of the measurements obtained from the different sensors.

The measurements used to estimate the oxidation-reduction potential are produced at different points of the pool since the different submersible robots necessarily occupy different positions (the accuracy is then directly linked to the number of robots used).

The reliability of the device is further enhanced when the submersible robots are configured to be submerged. There is then a guarantee that the measurements are produced at depth. Now, it has been proven that the measurements produced at depth are more representative of the quality of the water than those which are produced on the surface.

FIG. 2 represents a system according to a second embodiment of the invention. This system is a system for detecting intrusion capable of detecting the intrusion of a body in the water of the pool.

The sensors 150 capable of producing measurements of a quantity representative of a disturbance of the pool and, more specifically, of the liquid contained in the pool, relative to a reference state, are installed onboard each of the submersible robots 2A, 2B, 2C. In this embodiment, the disturbance is an intrusion of an individual in the pool.

The sensors 150 are, for example, capable of detecting an intrusion of a body, for example of an individual, in the pool.

In this embodiment, the sensors 150 are capable of detecting the intrusion of an individual in the liquid contained in the pool which is water in the example described.

They are, for example, capable of producing a measurement of a quantity which varies upon an intrusion of an individual in the liquid contained in the pool. The intrusion is, for example, detected if the quantity undergoes an abrupt variation, that is to say if the variation of the quantity during a predetermined time interval is above a predetermined threshold. The sensors 150 are, for example, capable of measuring brightness and of detecting an abrupt variation of this brightness. They can also be capable of detecting an intrusion when the brightness falls below a predetermined threshold.

The sensors 150 can also be of sound type, namely capable of detecting the shockwave created by the immersion and then the sound trace of the bubbles.

The sensors 150 are capable of producing probability signals representative of the probability with which the intrusion is likely to have occurred. The sensors are also capable of producing alert signals when they detect an intrusion, that is to say an immersion event.

For example, an alert signal is produced when the speed of the variation of the brightness is above a predetermined detection threshold and the probability signal associated with the alert signal is proportional to the speed of variation of the probability.

The alert and probability signals are sent to the second element which is, in FIG. 2, a floating central unit 5 and which has the processing means 11 installed on it.

A method of implementing the device according to the second embodiment of the invention will now be described.

Figure 3:
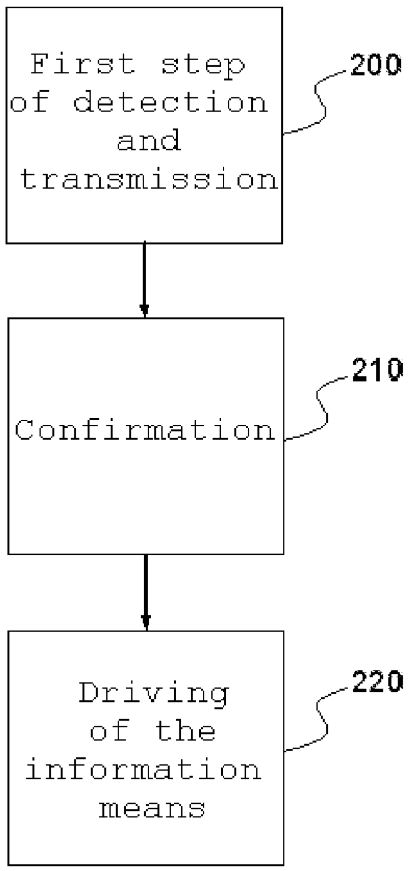
FIG. 3 represents the main steps of the method according to the invention.

The major steps of the method are represented in FIG. 3.

Implementing this method requires the system according to the second embodiment of the invention to comprise several submersible robots each with at least one sensor 150 installed on it.

The method comprises a first step 200 of detection of the intrusion of an individual in the water of the leisure pool upon which the sensors 150 produce, when they detect the falling of an individual in the water, a first alert signal A1 and a first probability signal PA1, PB1, PC1 representative of the probability with which the intrusion of an individual in the water of the pool is likely to have actually occurred. This step also comprises a step of transmission of the first signals to the processing means 11. Here, the data are transmitted to the second element which is the central processing unit 5.

When at least one first alert signal A1 is sent to the processing means 11 by a first submersible robot, the method comprises a confirmation step 210 consisting in checking, at least on the basis of a first probability signal from one or more second submersible robots that are different from the first submersible robot, whether the fall of an individual is confirmed by at least one second submersible robot.

This confirmation step makes it possible to improve the reliability of the device according to the invention compared to a device which would comprise a single detector. When an immersion event is confirmed by the device, the probability that the immersion has actually occurred is high. The confirmation step makes it possible to discriminate false detections.

If the intrusion is confirmed, the method comprises a step 220 of driving the information means by means of the processing means 11 so as to inform an individual of the occurrence of a fall of an individual into the water of the pool. This, for example, entails driving the alarm device in such a way as to emit an audible and/or visual alarm or else driving a display device so as to display information.

According to a preferred embodiment, the device according to the second embodiment comprises at least three submersible robots.

Figure 4:
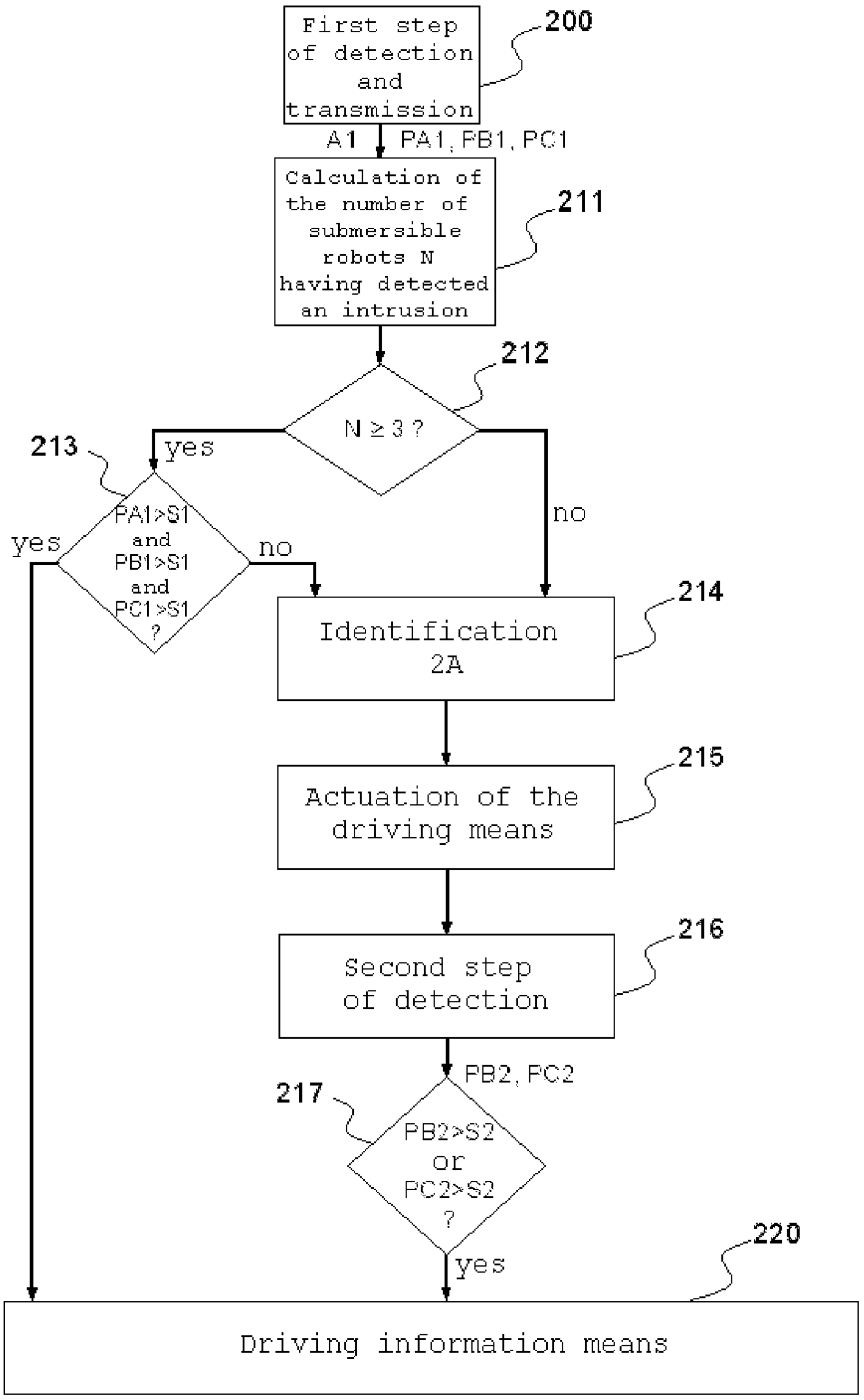
FIG. 4 represents the detailed steps of a preferred embodiment of the method according to the invention.

FIG. 4 schematically represents the steps of the method in this case.

The confirmation step 210 comprises a step 211 of calculating the number of submersible robots N having transmitted a first alert signal to the processing means 11 and a first step 212 of comparing the number of submersible craft N to a predetermined threshold number. This threshold number is equal to 3 in the example represented in FIG. 4.

Advantageously, this step consists in counting the number of submersible robots having transmitted a first alert signal Al to the processing means 11 within a predetermined time window.

If at least three submersible robots have detected an intrusion, then the confirmation step comprises a second step 213 of comparison of the first probability signals PA1, PB1, PC1 accompanying the first alert signals A1, with a first predetermined probability threshold S1.

If all the first probability signals PA1, PB1, PC1, associated with the respective first alert signals A1, are above the first predetermined threshold S1, the occurrence of the intrusion event is confirmed.

Otherwise, the confirmation step 210 also advantageously (but not mandatorily) comprises a step 214 of identification of a main submersible robot corresponding to the submersible robot 2A from which the first probability signal with the highest value was obtained.

Moreover, the confirmation step 210 comprises a step 215 of actuation of the driving means of the other submersible robots 2B, 2C corresponding to the submersible robots other than the main submersible robot 2A, so that they approach the main submersible robot 2A. This step is carried out by the actuation means on the basis of the measurements of the positions of the different submersible robots obtained from the location capabilities.

The confirmation step comprises a second detection step 216 during which the detection means 150 of the other submersible robots 2B, 2C produce second probability signals PB2, PC2 and transmit them to the processing means 11 via the wireless communication means 6.

This step is followed by a third step 217 of comparison of the second probability signals PB2, PC2 obtained from the other submersible robots with a second predetermined probability threshold S2. The immersion event is advantageously confirmed if at least one second probability signal PB2, PC2 from at least one other submersible robot 2B, 2C is above the second predetermined threshold S2.

As a variant, during the actuation phase 215, only some of the other submersible robots are directed toward the main submersible robot. The reliability of the detection is all the greater when the number of submersible robots directed toward the main robot is great.

If the processing means 11 receive first alert signals from fewer than three submersible robots, the confirmation step 210 does not comprise the first comparison step 213.

Given that the convergence of the other submersible robots 2B, 2C with the main submersible robot 2A is not instantaneous, the second probability threshold S2 is advantageously below the first threshold. In practice, the consequences of the intrusion of a body in the pool are attenuated over time. For example, in the case of the measurement of acoustic waves, the shockwave produced by the immersion event has time to be attenuated.

As a variant, the first probability threshold S1 is equal to the second probability threshold S2. This embodiment for example makes sense when the detection means are of optical type and the probability signals are inversely proportional to the brightness.

So as to implement the actuation step 215, the location capabilities of the submersible robots are advantageously used.

Figure 5:
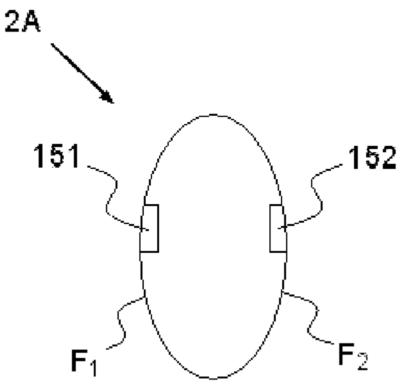
FIG. 5 represents an exemplary arrangement of sensors installed on a submersible robot.

Advantageously, as represented in FIG. 5, a sensor 150 installed onboard a submersible robot 2A comprises two individual sensors 151, 152 arranged in such a way as to be spaced apart from one another in a horizontal plane when the submersible craft is immersed. The system advantageously comprises means for detecting an area of immersion in which the immersion is assumed to have occurred on the basis of the signals from two individual sensors.

For example, the two individual sensors 151, 152 are arranged on the respective flanks F1, F2 of the submersible craft 2A. Advantageously, the submersible robot 2A has an oblong shape, in a horizontal plane, when the submersible craft is immersed.

The system according to the invention offers good reliability. In practice, the sensors capable of detecting an intrusion exhibit a better sensitivity when they are placed under the water than when they are placed on the surface.

So as to implement the method described previously, the processing means comprise the following means (which are not represented in FIG. 2):

- means for calculating the number of submersible craft N having detected an intrusion,
- means for comparing the number of submersible craft with the threshold number,
- means for comparing probability signals to a predetermined threshold so as to be able to implement the two comparison steps 213, 217,
- means for identifying the submersible craft having transmitted to the processing means the greatest probability signal.

These means are advantageously computation modules.

The system according to the invention is easy to install. It does not entail any installation operations on the pool. The sensors are notably mounted on a submersible robot outside the pool. The robot is then immersed in the water of the pool. The maintenance of the surveillance device is also eased.

In variants of the first and second embodiments of the invention, the first element consists of one or more submersible robots 2A, 2B, 2C as described previously. The second element also consists of a submersible robot 2A, 2B, 2C as described previously. The expression “master-slave robots” then applies. The system is then also configured to process, in the processing means, the outputs of the sensor or sensors 15, 150 installed onboard the second element and, if necessary, of the location capabilities of said second element.

The processing means 11 can be installed onboard the master robot (second element). They can also be remote and provided with communication capabilities for communicating with the second element (master robot). The master robot then receives the outputs of the sensors 15, 150 and, if appropriate, of the location capabilities of the slave robots and also of the master robot and transmits them to the processing means. In other words, in this case, the system comprises a set of robots comprising a first set of robots corresponding to the robots of the first element and an additional robot corresponding to the second element. This additional robot is the master robot and the robot(s) of the first element is(are) slave robot(s).

The actuation means 3 can be installed onboard the master robot.

Moreover, when the systems according to the first and second embodiments comprise a number of submersible robots, the latter can be distributed between the first and the second element. The first element can consist of one or more submersible robots as described previously and the second element can consist of a submersible robot as described previously.

The invention claimed is:

1. A method for surveilling a pool containing water on the basis of:

- a plurality of submersible robots provided with wireless link means for communicating, in the submerged position, with at least one second element, said second element being one of said plurality of robots or a central unit configured to float on the liquid contained in said pool, and
- sensors capable of detecting at least one disturbance of said pool relative to a reference state being installed onboard said submersible robots;

said method comprising:

- a step of detecting at least one disturbance of said pool relative to a reference state, said measurements being obtained from said sensors, a step of communication of said first element in the submerged position with at least one second element, a step of processing of the outputs of said sensors, to trigger at least one action of information on the disturbance of the pool relative to a reference state by means of information means, and
- a step of detecting an intrusion of a body in the water in which at least one sensor of said sensors produces, when detecting the intrusion of an individual in the water, a first alert signal A1 and a first probability signal PA1, PB1, PC1 representative of the probability with which the intrusion is likely to have really actually occurred,
- and, when a first alert signal A1 is produced by a first submersible robot, a confirmation step upon which a check is carried out, at least on the basis of a probability signal from at least one second submersible robot, as to whether the intrusion of an individual is confirmed by at least one second submersible robot.

2. The surveillance method as claimed in claim 1, comprising, when the intrusion is confirmed, a step of driving information means so as to inform an individual of the occurrence of a fall by an individual into the water of the pool.

3. The surveillance method as claimed in claim 1, in which the confirmation step comprises:

- a first step of comparison of the number of submersible robots N having produced a first alert signal A1 with a predetermined threshold number,
- and, when the number of submersible robots N having produced a first alert signal A1 is at least equal to the predetermined threshold number, a second step of comparison of first probability signals PA1, PB1, PC1, associated with the respective alert signals A1, with a first predetermined probability threshold S1.

4. The surveillance method as claimed in claim 3, in which the confirmation step comprises, when at least one probability signal is below the first predetermined threshold, respectively when the number of submersible robots having produced a first alert signal A1 is less than the predetermined threshold number,

- a step of identification of a main submersible robot corresponding to the submersible robot from which the first probability signal with the highest value is obtained,
- a step of actuation of the driving means of at least one other submersible robot, corresponding to a submersible robot other than the main submersible robot, so that it approaches the main submersible robot, a second detection step during which a sensor installed onboard said at least one other submersible robot produces a probability signal representative of the probability with which the intrusion is likely to have really occurred, a third comparison step during which said at least one second probability signal is compared with a second probability threshold.

5. The surveillance method as claimed in claim 4, in which the intrusion event is confirmed when at least one second probability signal is above the second predetermined threshold.

6. The surveillance method as claimed in claim 4, in which the threshold number is equal to three.

* * * * *